(12) United States Patent
Saito et al.

(10) Patent No.: US 6,612,698 B2
(45) Date of Patent: Sep. 2, 2003

(54) PUPIL MEASUREMENT APPARATUS, REFRACTION CORRECTION APPARATUS, AND PUPIL MEASUREMENT METHOD

(75) Inventors: Seiji Saito, Hokkaido (JP); Shuichiro Eguchi, Hokkaido (JP); Yasuko Ise, Hokkaido (JP)

(73) Assignee: Explorer Inc., Hokkaido (JP)

( * ) Notice: Subject to any disclaimer, the term of this patent is extended or adjusted under 35 U.S.C. 154(b) by 36 days.

(21) Appl. No.: 10/053,916

(22) Filed: Jan. 24, 2002

(65) Prior Publication Data

US 2002/0097378 A1 Jul. 25, 2002

(30) Foreign Application Priority Data

Jan. 25, 2001 (JP) .......................................... 2001-017477

(51) Int. Cl.[7] ................................................. A61B 3/14
(52) U.S. Cl. ....................................................... 351/210
(58) Field of Search ................................ 351/200, 204, 351/205, 206, 208, 209, 210, 221

(56) References Cited

U.S. PATENT DOCUMENTS 6,113,237 A * 9/2000 Ober et al. ................. 351/210
6,152,564 A * 11/2000 Ober et al. ................. 351/210

OTHER PUBLICATIONS

Nikkei Snagyo Shimbun, Sep. 20, 2000 (Translation) Explorer Inc. measure pupil movement, for medical treatment and security.

Nihon Keizai Shinmbun, Sep. 13, 2000 (Translation) Explorer Inc. developed pupil measurement apparatus, applicable for check system.

* cited by examiner

*Primary Examiner*—George Manuel
(74) *Attorney, Agent, or Firm*—Arent Fox Kintner Plotkin & Kahn, PLLC

(57) ABSTRACT

A video imaging device obtains the eyeball image of a cornea using light emitted from an imaging light source to the cornea. On the basis of the obtained eyeball image, a video processing device calculates the X- and Y-axis shift amounts and torsion angle of the cornea with respect to the reference position and causes a coordinate indicating device to indicate the calculated X- and Y-axis shift amounts and torsion angle. With this arrangement, the position and torsion angle of the cornea of the patient can be accurately detected and measured without forming any mark on the eyeball to measure the position of the cornea, and the measured position and torsion angle of the cornea can be indicated.

18 Claims, 16 Drawing Sheets

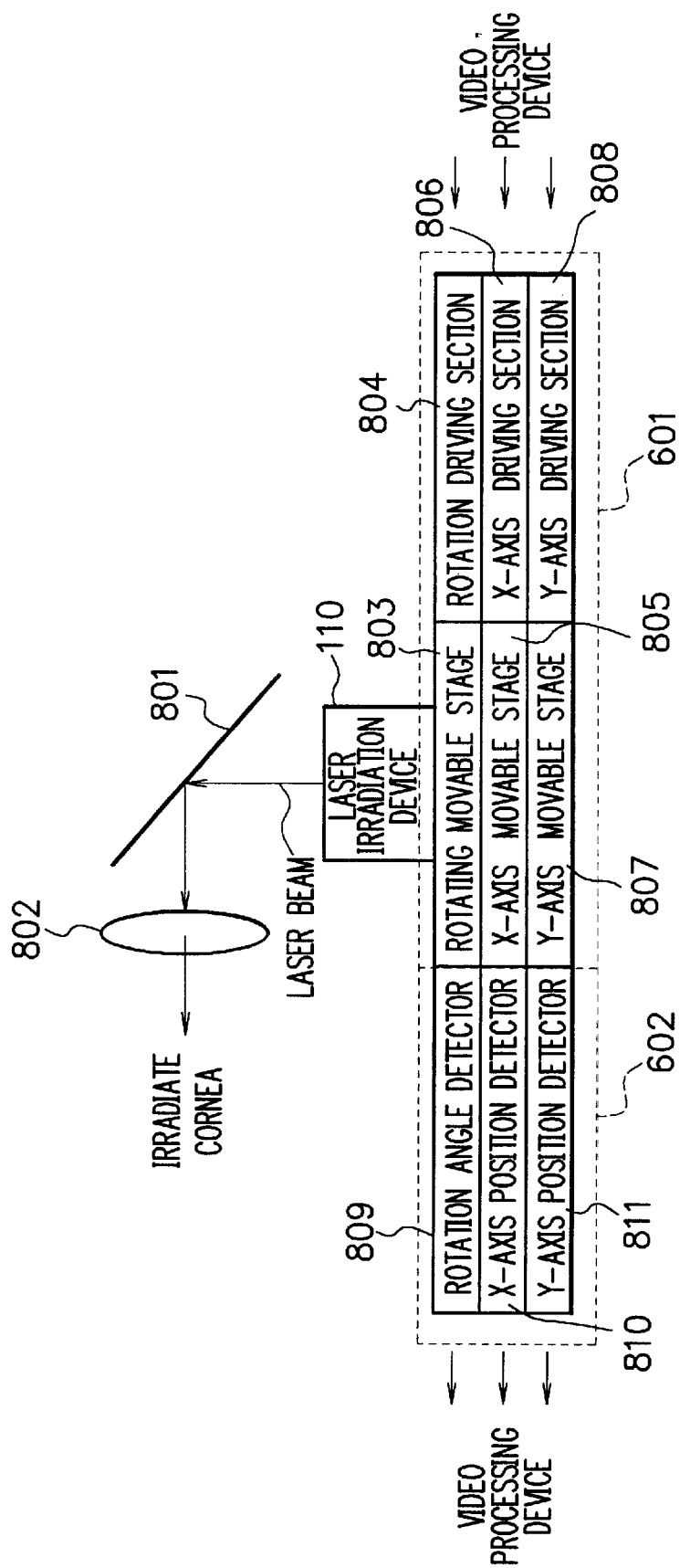

POINT B: AFTER CORRECTION

POINT A: BEFORE CORRECTION

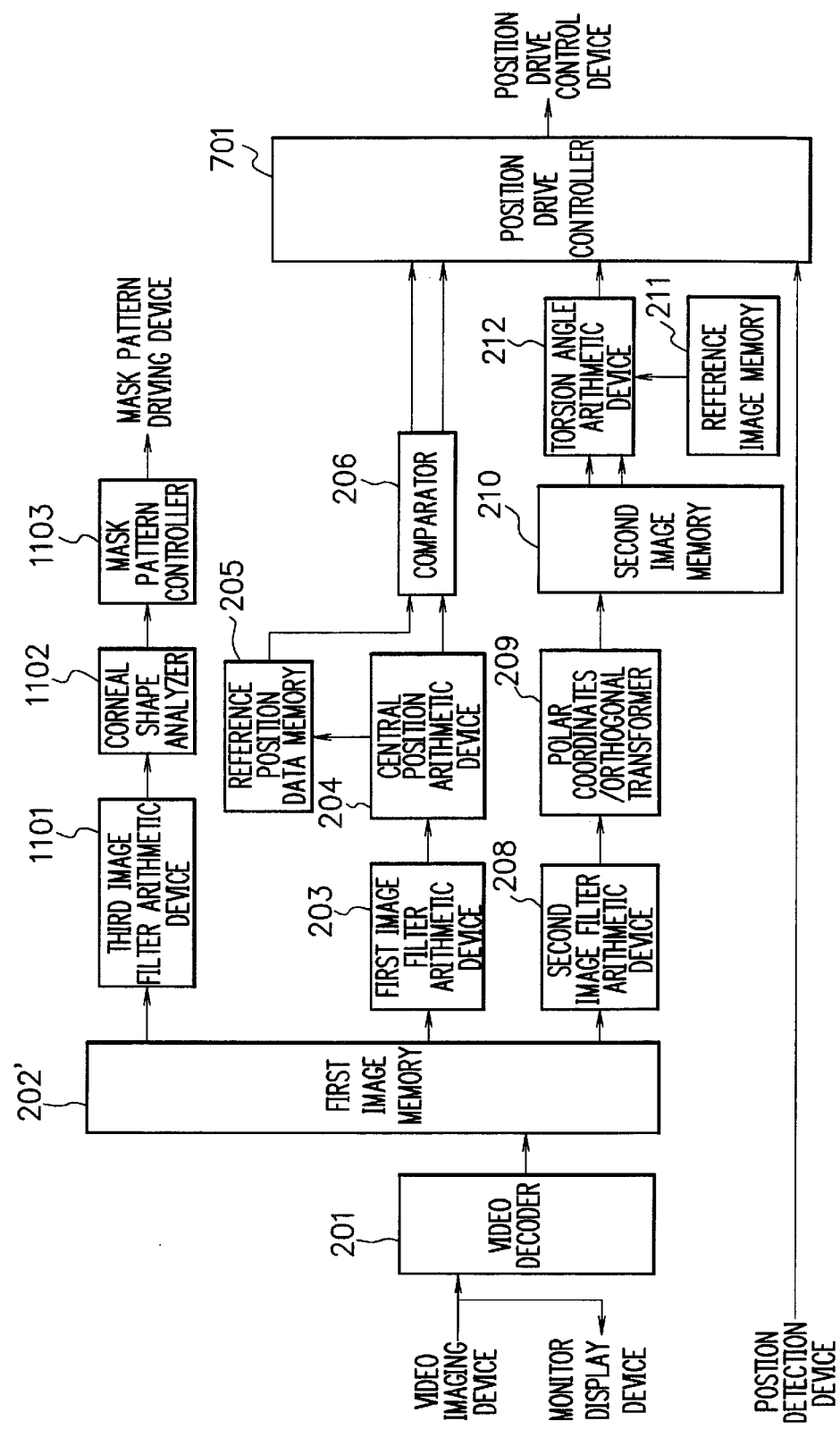

F I G. 12A
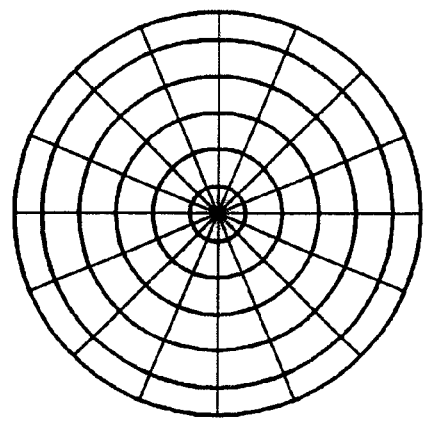
F I G. 12B
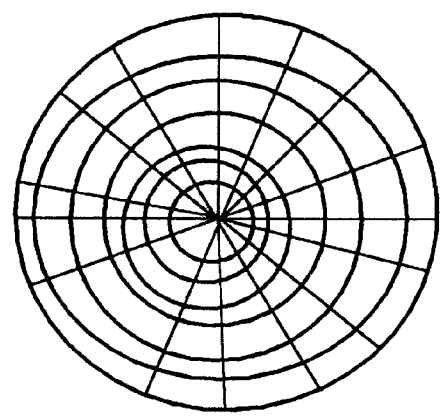

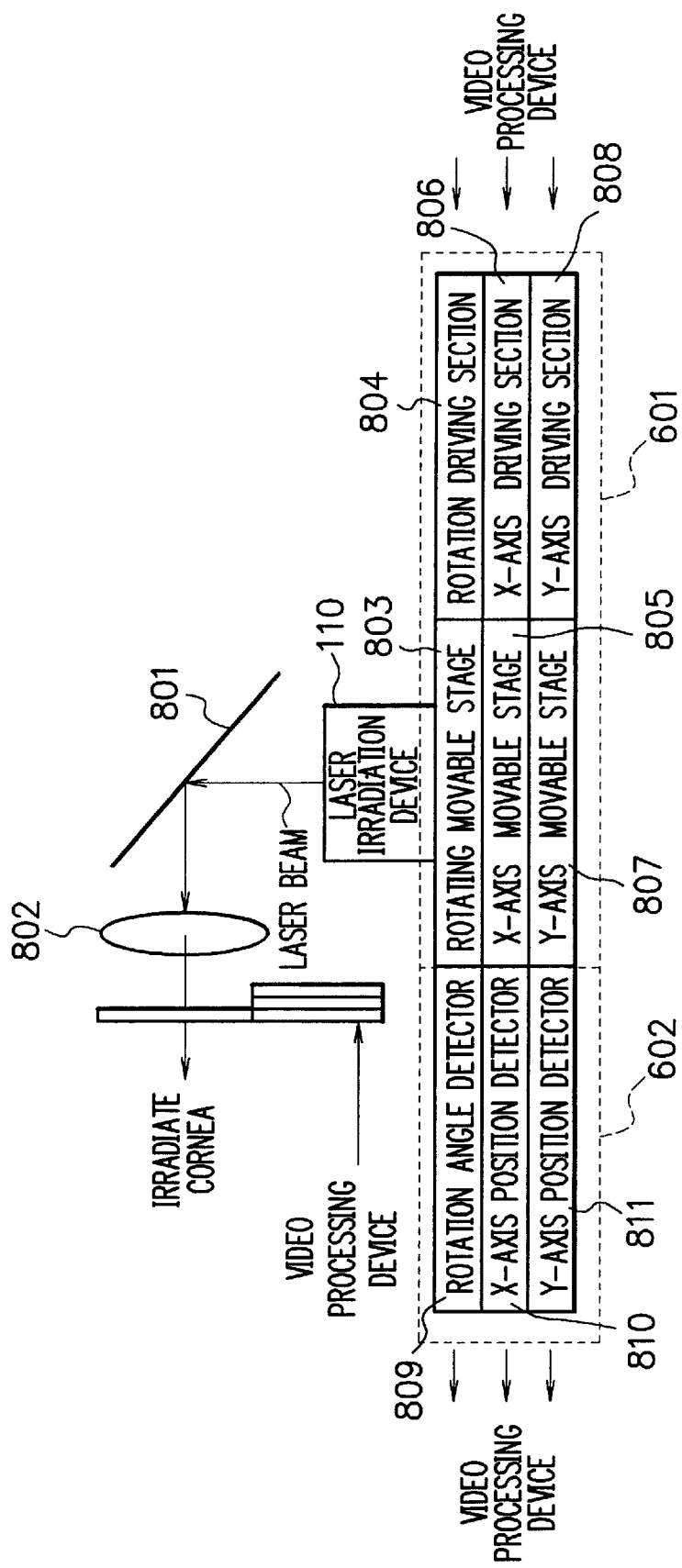

PUPIL MEASUREMENT APPARATUS, REFRACTION CORRECTION APPARATUS, AND PUPIL MEASUREMENT METHOD

CROSS-REFERENCE TO RELATED APPLICATIONS

This application is based upon and claims priority of Japanese Patent Application No. 2001-017477, filed on Jan. 25, 2001, the contents being incorporated herein by reference.

BACKGROUND OF THE INVENTION

1. Field of the Invention

The present invention relates to a pupil measurement apparatus, refraction correction apparatus, and pupil measurement method and, more particularly, to a visual function correction apparatus which irradiates a cornea with a laser beam to correct the corneal shape and correct refraction.

2. Description of the Related Art

Conventionally, refraction correction surgeries such as LASIK (LAser in SItu Keratomileusis) are used to correct refraction, in which a cornea is irradiated with an excimer laser to change the corneal shape (e.g., the radius of curvature or distortion), i.e., to change the refracting power of the cornea, thereby correcting the refraction. In LASIK, the surface of the cornea of an eyeball is stripped off thin by an electric knife. Then, the cornea is shaved by irradiating it with an excimer laser. Finally, the stripped corneal surface is returned to the original position, thereby correcting the corneal shape for refraction correction.

For example, near-sightedness occurs because the radius of curvature of a cornea is small, and an image is formed before a retina. To correct the near-sightedness, the cornea is uniformly shaved to increase its radius of curvature, i.e., to make the cornea flatter to correct the visual acuity. Hence, to correct near-sightedness, the cornea is irradiated with a laser beam such that a round laser beam irradiation region is formed.

Additionally, for example, astigmatism occurs because the corneal shape is nonuniform and distorted due to, e.g., the index distribution depending on the elliptical direction of the corneal lens of an eye. To correct the astigmatism, the cornea is shaved to change the radius of curvature at each position of it, thereby correcting the visual acuity.

Hence, to correct near-sightedness including astigmatism when a cornea has, e.g., an elliptical distortion, the cornea is irradiated with a laser beam such that the laser beam irradiation region has an elliptical shape having a major axis perpendicular to the major axis of the elliptical distortion to make the corneal shape uniform.

FIG. 16 is a block diagram showing the arrangement of a conventional refraction correction apparatus which irradiates a cornea with a laser beam to change the corneal shape for visual acuity correction.

Referring to FIG. 16, a cornea 1604 of an eyeball 1603 is irradiated, through a half mirror 1602, with light emitted from an imaging light source 1601. The irradiation light is reflected by the cornea 1604 and supplied to a microscope 1605 and video imaging device 1606 through the half mirror 1602.

The cornea 1604 is enlarged and observed with the microscope 1605. Simultaneously, the image of the cornea 1604 is obtained by the video imaging device 1606, and the obtained image of the cornea 1604 is displayed on a monitor display device 1607.

For, e.g., near-sightedness correction surgery, the operator strips off a thin surface of the cornea 1604 of the patient using an electric knife. Then, the operator observes marks formed on the eyeball (iris) of the patient in advance with the microscope 1605 and aligns the position of the cornea 1604 with the laser beam irradiation position. When alignment between the position of the cornea 1604 and the laser beam irradiation position is ended, the cornea 1604 is irradiated with a laser beam from a laser irradiation device 1608 through the half mirror 1602 to shave the cornea, thereby correcting refraction.

However, when refraction correction surgery is done using the above-described conventional refraction correction apparatus, marks must be formed on the eyeball (conjunctival portion) of the patient, and the position of the cornea 1604 and the laser beam irradiation position must be aligned while checking the marks with the microscope 1605. Hence, the operator requires a skill.

Especially, to correct near-sightedness including astigmatism, the cornea 1604 is irradiated with a laser beam with an elliptical irradiation region in refraction correction surgery. Unless the position of the cornea 1604 and the position of the laser beam are accurately aligned in the direction of rotational axis, the cornea 1604 is not correctly irradiated with the laser beam, and the astigmatism cannot be accurately corrected.

Furthermore, since the eyeball of the patient does not stand still during refraction correction surgery, the laser beam irradiation position and the position of the cornea 1604 shift in the directions of X- and Y-axes and rotational axis. Hence, accurate refraction correction surgery is impossible.

The above problems will be described below with reference to FIGS. 17A, 17B, 18A, and 18B.

FIGS. 17A and 17B are views for explaining the position of the cornea 1604 and a laser beam irradiation position 1701 in refraction correction surgery for correcting near-sightedness. When the position of the cornea 1604 and the laser beam irradiation position 1701 are correctly aligned, the center of the laser beam irradiation position 1701 matches the center of the cornea 1604, as shown in FIG. 17A. Hence, a desired portion of the cornea 1604 can be shaved to accurately correct near-sightedness.

On the other hand, if the position of the cornea 1604 and the laser beam irradiation position 1701 are not correctly aligned, the center of the laser beam irradiation position 1701 shifts from the center of the cornea 1604, as shown in FIG. 17B. Hence, a desired portion of the cornea 1604 cannot be shaved, and consequently, near-sightedness cannot be accurately corrected.

FIGS. 18A and 18B are views for explaining the position of the cornea 1604 and a laser beam irradiation position 1801 in refraction correction surgery for correcting near-sightedness including astigmatism. When the position of the cornea 1604 and the laser beam irradiation position 1801 are correctly aligned, a desired position of the cornea 1604 can be irradiated with the laser beam, as shown in FIG. 18A. Hence, the astigmatism can be accurately corrected.

On the other hand, if the position of the cornea 1604 and the laser beam irradiation position 1801 are not correctly aligned, a desired position of the cornea 1604 cannot be irradiated with the laser beam, as shown in FIG. 18B. Hence, the astigmatism cannot be accurately corrected. Especially, in the refraction correction surgery for correcting near-sightedness including astigmatism, as shown in FIG. 18B, if the major axis of the ellipse to be irradiated with the laser beam does not match the major axis of the elliptical laser beam irradiation region due to the torsion of the eyeball, the astigmatism cannot be accurately corrected, though the position of the cornea 1604 matches the central position of the laser beam irradiation position 1801.

SUMMARY OF THE INVENTION

The present invention has been made to solve the above problems, and has as its object to make it possible to accurately measure the position and torsion angle of a cornea without forming any mark on an eyeball to measure the position of the cornea.

It is another object of the present invention to provide a refraction correction apparatus capable of easily and accurately aligning the position of a cornea and a laser beam irradiation position without forming any mark on an eyeball of a patient to align the position of the cornea and the laser beam irradiation position.

According to an aspect of the present invention, there is provided a pupil measurement apparatus comprising an imaging unit for obtaining an image of an eyeball, an arithmetic processing unit for calculating a position and torsion angle of a pupil in the eyeball on the basis of the eyeball image obtained by the imaging unit, and an indicating unit for indicating pieces of information related to the position and torsion angle of the pupil and output from the arithmetic processing unit.

According to another aspect of the present invention, there is provided a pupil measurement apparatus comprising an imaging unit for obtaining an image of an eyeball, an arithmetic processing unit for calculating a position and torsion angle of a pupil in the eyeball on the basis of the eyeball image obtained by the imaging unit, and a storage unit for storing pieces of information related to the position and torsion angle of the pupil and output from the arithmetic processing unit.

According to still another aspect of the present invention, there is provided a pupil measurement apparatus comprising an imaging unit for obtaining an image of an eyeball, a coordinate conversion unit for executing polar coordinates/orthogonal transform processing for the eyeball image obtained by the imaging unit, and an arithmetic processing unit for comparing the eyeball image orthogonally transformed by the coordinate conversion unit with a reference eyeball image stored in advance to calculate a position and torsion angle of a pupil in the eyeball.

A refraction correction apparatus of the present invention has one of the above-mentioned pupil measurement apparatuses.

According to still another aspect of the present invention, there is provided a pupil measurement method wherein an image of an eyeball is obtained, a position and torsion angle of a pupil in the eyeball are calculated on the basis of the obtained eyeball image, and pieces of information related to the calculated position and torsion angle of the pupil are indicated.

According to still another aspect of the present invention, there is provided a pupil measurement method wherein an image of an eyeball is obtained, a position and torsion angle of a pupil in the eyeball are calculated on the basis of the obtained eyeball image, and pieces of information related to the calculated position and torsion angle of the pupil are stored.

According to still another aspect of the present invention, there is provided a pupil measurement method wherein an image of an eyeball is obtained, polar coordinates/orthogonal transform processing is executed for the obtained eyeball image, and pieces of the orthogonally transformed eyeball image is compared with a reference eyeball image stored in advance to calculate a position and torsion angle of a pupil in the eyeball.

According to the present invention with the above arrangements, on the basis of an obtained eyeball image, the position and torsion angle of a pupil in the eyeball are calculated, and pieces of information related to the calculated position and torsion angle of the pupil are indicated or stored. Hence, the position and torsion angle of a cornea can be accurately measured by executing arithmetic processing for the eyeball image obtained from the eyeball without forming any mark on the eyeball to measure the position of the cornea or pupil in the eyeball.

Additionally, on the basis of the obtained eyeball image, the pieces of information related to the calculated position and torsion angle of the pupil are indicated or stored. When the pupil measurement apparatus is used for a refraction correction apparatus, the position of the cornea and the laser beam irradiation position can easily be accurately aligned.

BRIEF DESCRIPTION OF THE DRAWINGS

FIG. 8 is a view showing the arrangements of a laser irradiation device, position drive control device, and position detection device;

FIG. 11 is a block diagram showing the detailed arrangement of a video processing device;

FIGS. 12A and 12B are views showing contour lines by a corneal shape;

FIG. 13 is a view showing the arrangements of a laser irradiation device, position drive control device, position detection device, mask pattern drive control device, and mask pattern;

DETAILED DESCRIPTION OF THE PREFERRED EMBODIMENTS

The embodiments of the present invention will be described below with reference to the accompanying drawings.

(First Embodiment)

Figure 1:
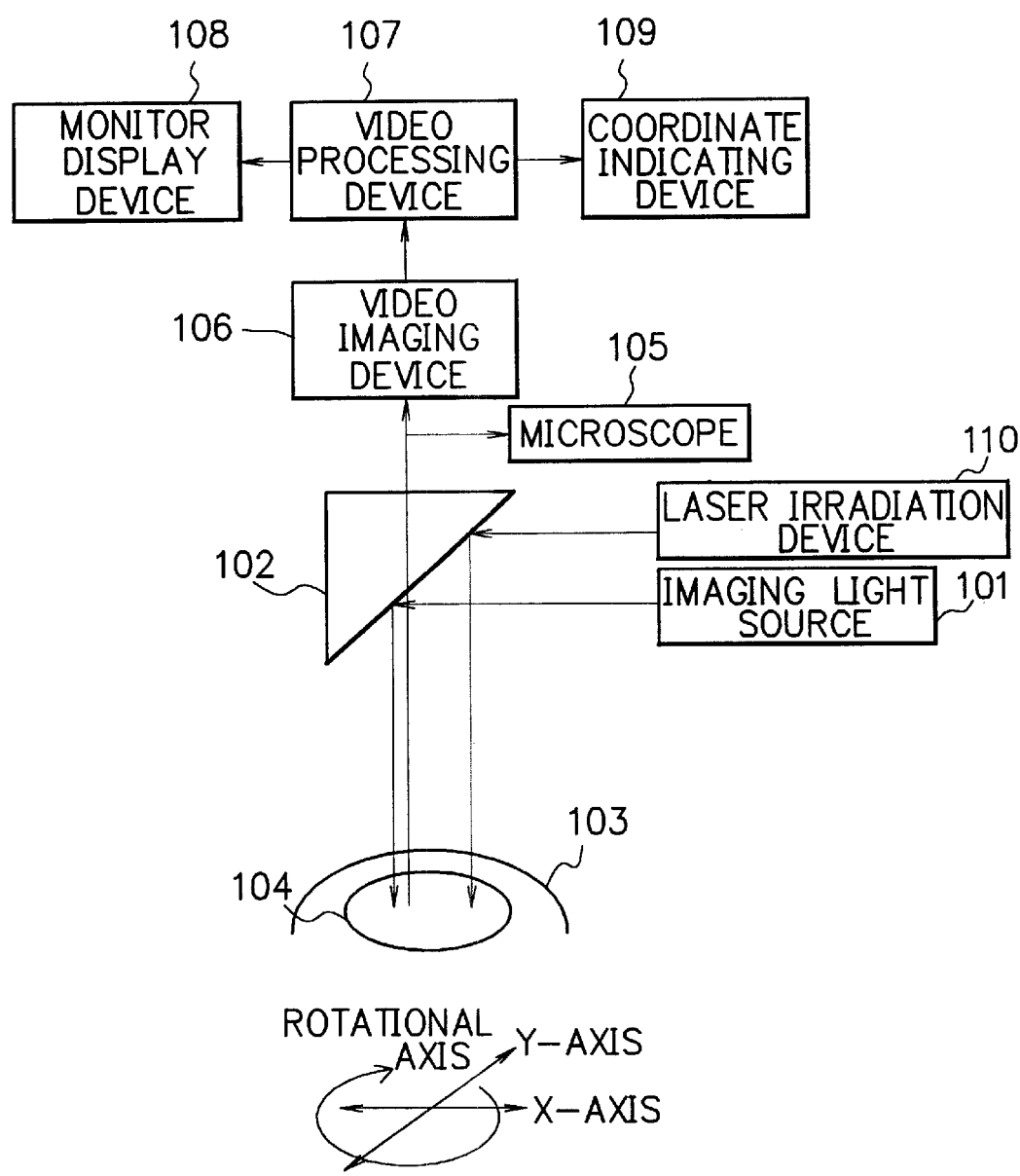
FIG. 1 is a block diagram showing the arrangement of a refraction correction apparatus to which a pupil measurement apparatus according to the first embodiment is applied.

FIG. 1 is a block diagram showing the arrangement of a refraction correction apparatus to which a pupil measurement apparatus according to the first embodiment is applied.

Referring to FIG. 1, a cornea 104 of an eyeball 103 is irradiated, through a half mirror 102, with light emitted from an imaging light source 101. The irradiation light is reflected by the cornea 104 and supplied to a microscope 105 and a video imaging device 106 constituted by a CCD and the like through the half mirror 102. The cornea 104 is enlarged and observed with the microscope 105.

Simultaneously, the video imaging device 106 to which the reflected light from the cornea 104 is supplied through the half mirror 102 obtains the image of the cornea 104 and supplies the video signal of the obtained image of the cornea 104 to a video processing device 107. The video imaging device 106 has a CCD and the like.

The video processing device 107 supplies the video signal of the cornea 104, which is supplied from the video imaging device 106, to a monitor display device 108. The video processing device 107 also executes predetermined arithmetic processing for the video signal to calculate difference information of the cornea 104 with respect to the reference position and supplies the calculated difference information to a coordinate indicating device 109.

The difference information contains X- and Y-axis shift amounts and shift amount of the rotation angle of the cornea 104 with respect to the reference position. As shown in FIG. 1, the X-axis direction is a predetermined direction. The Y-axis direction is perpendicular to the X-axis direction. The rotation angle is an angle in the direction of rotational axis on the X-Y plane.

The monitor display device 108 displays the image of the cornea 104 on the basis of the video signal of the cornea 104, which is supplied from the video processing device 107. The coordinate indicating device 109 indicates the pieces of difference information (shift amounts) of the cornea 104 with respect to the reference position, which are supplied from the video processing device 107. The coordinate indicating device 109 is formed from an indicating device such as a 7-segment LED capable of indicating a numerical value.

With this arrangement, for, e.g., refraction correction surgery, the operator strips a thin surface of the cornea 104 of a patient using an electric knife and then aligns the position of the cornea 104 and the laser beam irradiation position by moving the patient until the values of the pieces of difference information (shift amounts) of the cornea 104 with respect to the reference position, which are indicated by the coordinate indicating device 109, become "0" or adjusting the position of a laser irradiation device 110 while seeing the difference information. When alignment between the position of the cornea 104 and the laser beam irradiation position is ended, the cornea is shaved by irradiating the cornea 104 with a laser beam from the laser irradiation device 110 through the half mirror 102, thereby correcting refraction.

Figure 2:
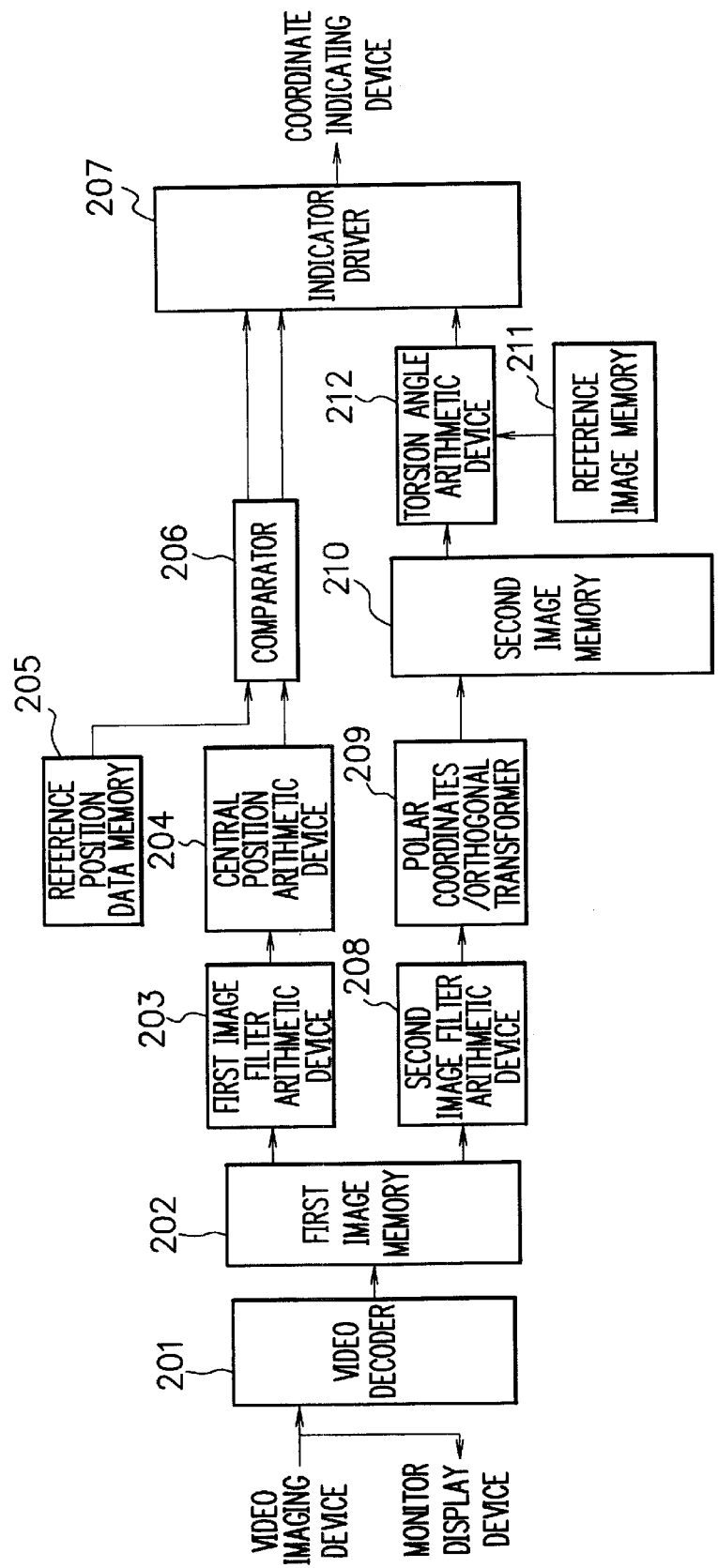
FIG. 2 is a block diagram showing the detailed arrangement of a video processing device.

FIG. 2 is a block diagram showing the detailed arrangement of the video processing device 107 shown in FIG. 1.

Referring to FIG. 2, the video signal of the cornea 104, which is supplied from the video imaging device 106, is output to the monitor display device 108 and also supplied to a video decoder 201.

Upon receiving the video signal of the cornea 104, the video decoder 201 executes predetermined processing for the video signal to separate the video signal into a sync signal and image signal. The video decoder 201 supplies, as image data, the image signal obtained by separating the video signal to a first image memory 202 and causes it to store the image signal. The image data stored in the first image memory 202 is supplied to first and second image filter arithmetic devices 203 and 208.

The image data stored in the first image memory 202 is supplied to the first image filter arithmetic device 203 having a filter and the like. The first image filter arithmetic device 203 executes image processing such as noise removal and spatial filter. The image data that has undergone image processing by the first image filter arithmetic device 203 is supplied to a central position arithmetic device 204.

Upon receiving the image data that has undergone the image processing, the central position arithmetic device 204 calculates the X- and Y-coordinates of the central position of the pupil (cornea) on the basis of the image data that has undergone image processing and supplies a calculation result to a comparator 206. The X- and Y-coordinates of the central position of the pupil (cornea), which are supplied by the central position arithmetic device 204 and supplied to the comparator 206, are compared by the comparator 206 with the position data of the pupil (cornea) stored in a reference position data memory 205 in advance.

The comparator 206 calculates, as a comparison result, difference value data between the X- and Y-coordinates of the central position of the pupil (cornea) based on the image data and the position data of the pupil (cornea) stored in the reference position data memory 205 and supplies the difference value data to an indicator driver 207.

Upon receiving the difference value data from the comparator 206, the indicator driver 207 converts the received difference value data into indication data to be indicated by the coordinate indicating device 109 shown in FIG. 1 and supplies the data to the coordinate indicating device 109.

On the other hand, the image data stored in the first image memory 202 is supplied to the second image filter arithmetic device 208 having a filter and the like. The second image filter arithmetic device 208 executes image processing such as noise removal and spatial filter. The image data that has undergone image processing by the second image filter arithmetic device 208 is supplied to a polar coordinates/orthogonal transformer 209.

Upon receiving the image data that has undergone image processing, the polar coordinates/orthogonal transformer 209 converts the received image data from polar coordinates to orthogonal coordinates to execute processing by a torsion angle arithmetic device 212 connected to the output side through a second image memory 210. The image data orthogonally converted into orthogonal coordinates by the polar coordinates/orthogonal transformer 209 is supplied to and stored in the second image memory 210.

The image data stored in the second image memory 210 is supplied to the torsion angle arithmetic device 212. The torsion angle arithmetic device 212 performs predetermined arithmetic operation to execute correlation processing with image data stored in a reference image memory 211 in advance, thereby calculating the torsion angle with respect to the image data stored in the reference image memory 211 in advance.

In the correlation processing, the correlation value between the image data stored in the second image memory 210 and image data obtained by rotating the image data stored in the reference image memory 211 in advance about the rotational axis through a predetermined rotation angle is calculated for each of a plurality of rotation angles using a mutual correlation function. As a consequence, the value of a rotation angle at which the correlation value is maximized is calculated as a torsion angle.

The torsion angle calculated by the torsion angle arithmetic device 212 is supplied to the indicator driver 207, converted by the indicator driver 207 into indication data to be indicated by the coordinate indicating device 109 shown in FIG. 1, and supplied to the coordinate indicating device 109.

Figure 3:
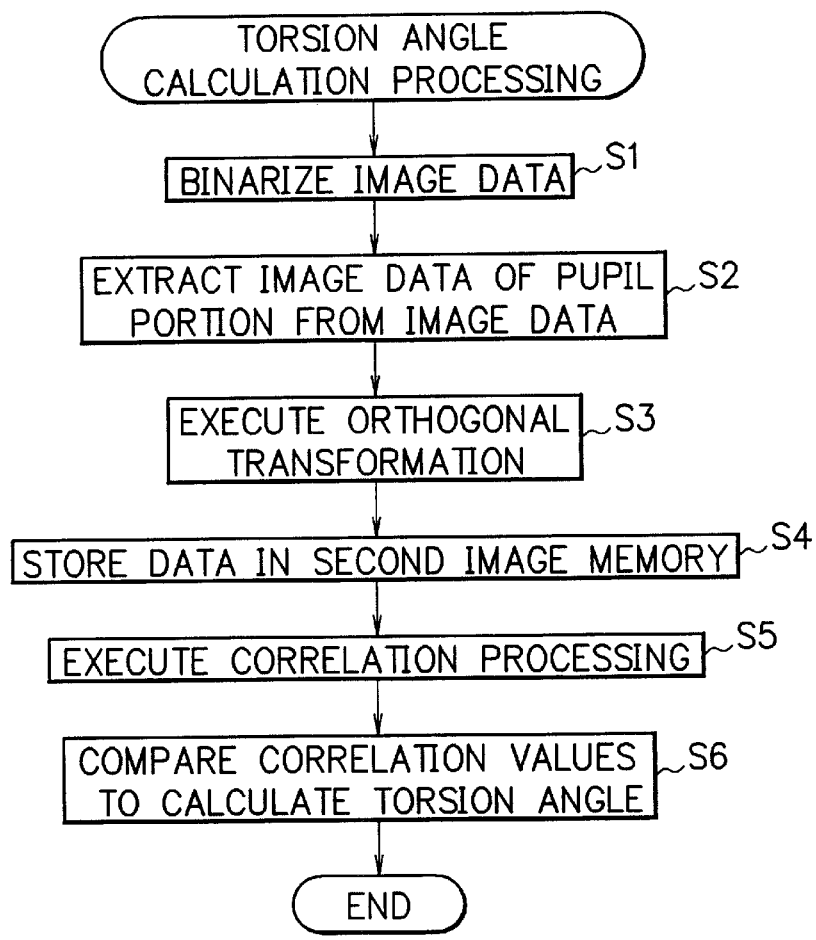
FIG. 3 is a flow chart showing the detailed flow of torsion angle calculation processing.

FIG. 3 is a flow chart showing the detailed flow of torsion angle calculation processing executed by the polar coordinates/orthogonal transformer 209, second image memory 210, reference image memory 211, and torsion angle arithmetic device 212.

Referring to FIG. 3, in step S1, the polar coordinates/orthogonal transformer 209 binarizes image data that has undergone image processing by the second image filter arithmetic device 208. In step S2, the polar coordinates/orthogonal transformer 209 projects the image data binarized in step S1 in the X- and Y-axis directions, obtains the central coordinates (X- and Y-coordinates) of the pupil and the size of the pupil, and, on the basis of these values, extracts only image data in the image region of the pupil from the image data.

In step S3, the polar coordinates/orthogonal transformer 209 executes polar coordinates/orthogonal transform processing for the image data of the pupil portion extracted in step S2 with reference to the center of the pupil and the X-axis (rotation angle: 0°). In step S4, the polar coordinates/orthogonal transformer 209 stores the image data after polar coordinates/orthogonal transform processing in the second image memory 210.

In step S5, the torsion angle arithmetic device 212 performs correlation processing using reference image data stored in the reference image memory 211 in advance and the image data stored in the second image memory 210. This correlation processing is performed by calculating, for each of a plurality of rotation angles, a correlation value by the mutual correlation function between the image data stored in the second image memory 210 and image data obtained by rotating the image data stored in the reference image memory 211 in advance through a predetermined rotation angle. In step S6, the correlation values calculated in step S5 are compared to obtain coordinates at which the correlation value is maximized. A torsion angle is obtained from the coordinate values.

Figure 4:
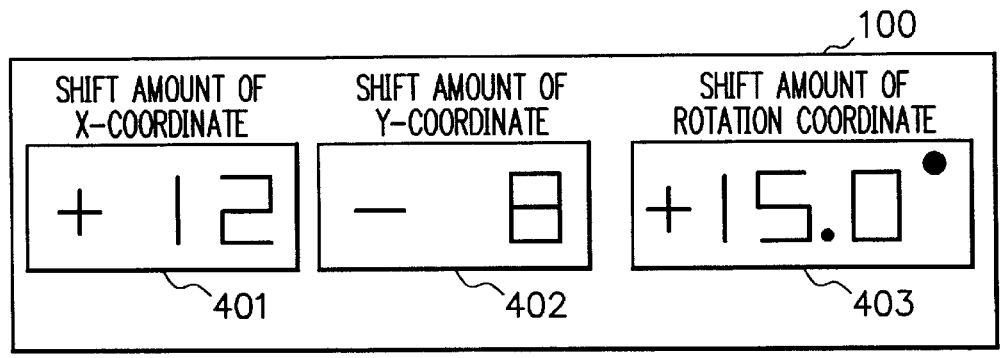
FIG. 4 is a view showing an indication example of difference information of a cornea with respect to the reference position by a coordinate indicating device.

An indication example of difference information (shift amounts) of the cornea 104 with respect to the reference position obtained in the above way is shown in FIG. 4.

FIG. 4 is a view showing an indication example of difference information (shift amounts) of the cornea 104 with respect to the reference position by the coordinate indicating device 109.

As shown in FIG. 4, the coordinate indicating device 109 has an indicator 401 for indicating the shift amount of the X-coordinate (X-axis direction), an indicator 402 for indicating the shift amount of the Y-coordinate (Y-axis direction), and an indicator 403 for indicating the shift amount of the rotation coordinate (rotational axis direction).

Referring to FIG. 4, for example, "+12" is indicated on the indicator 401 that indicates the shift amount of the X-coordinate (X-axis direction), and "−8" on the indicator 402 that indicates the shift amount of the Y-coordinate (Y-axis direction). In addition, "+15.0°" is indicated on the indicator 403 that indicates the shift amount of the rotation coordinate (rotational axis direction).

Figure 5:
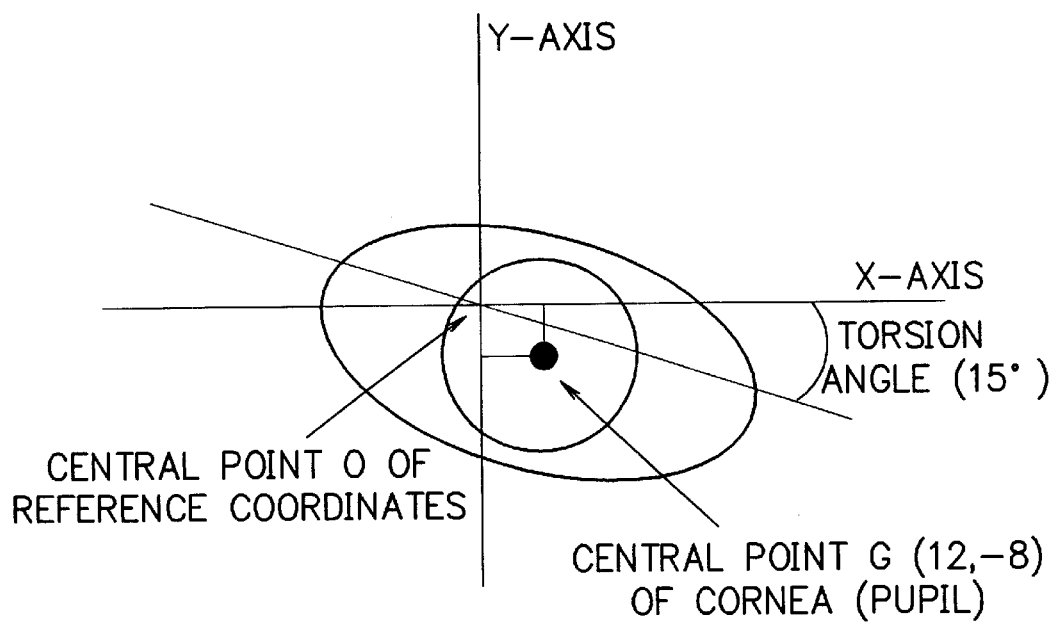
FIG. 5 is a view for explaining a shift between the position of a cornea and indication position by the coordinate indicating device.

At this time, the coordinate indicating device 109 indicates that the shift of the cornea 104 with respect to the reference position is 12 mm in the positive direction of the X-axis and −8 mm in the negative direction of the Y-axis, as shown in FIG. 5. The coordinate indicating device 109 also indicates that the cornea rotates about a point 12 mm in the positive direction of the X-axis and −8 mm in the negative direction of the Y-axis through 15° in the rotational axis direction (counterclockwise).

As described above, in accordance with the shifts of the cornea 104 with respect to the reference position, which are indicated by the coordinate indicating device 109, the operator moves and adjusts the patient such that the shift amounts on the coordinate indicating device 109 become zero.

As shown in FIG. 4, the coordinate indicating device 109 indicates each shift amount of the cornea 104 with respect to the reference position as a numerical value. However, a display device such as the monitor display device 108 capable of displaying an eyeball image may be used in place of the coordinate indicating device 109 such that the shift and direction of the cornea 104 with respect to the reference position can easily be visually recognized, as shown in FIG. 5.

As described above in detail, according to this embodiment, the video imaging device obtains the eyeball image of the cornea 104 using light emitted from the imaging light source 101 to the cornea 104. On the basis of the obtained eyeball image, the video processing device 107 calculates the X- and Y-axis shift amounts and torsion angle of the cornea 104 with respect to the reference position and causes the coordinate indicating device 109 to indicate the calculated X- and Y-axis shift amounts and torsion angle.

With this arrangement, in refraction correction surgery by the refraction correction apparatus, the position and torsion angle of the cornea of a patient can be accurately detected without forming any mark on the eyeball of the patient to measure the position of the cornea 104, and the operator can easily grasp the shift between the cornea 104 of the patient and the irradiation position of a laser beam for shaving the cornea 104. Hence, the operator can do easy adjustment to make the position of the cornea of the patient match the laser beam irradiation position only by checking the X- and Y-axis shift amounts and torsion angle indicated by the coordinate indicating device 109.

(Second Embodiment)

The second embodiment of the present invention will be described next.

In the second embodiment, a refraction correction apparatus performs automatic adjustment on the basis of pieces of difference information (shift amounts) of a cornea 104 with respect to the reference position such that the pieces of difference information become "0", unlike the first embodiment in which an operator who is seeing pieces of difference information (shift amounts) of the cornea 104 with respect to the reference position, which are indicated by the coordinate indicating device 109, moves and adjusts the position of a patient such that the pieces of difference information (shift amounts) become "0".

Figure 6:
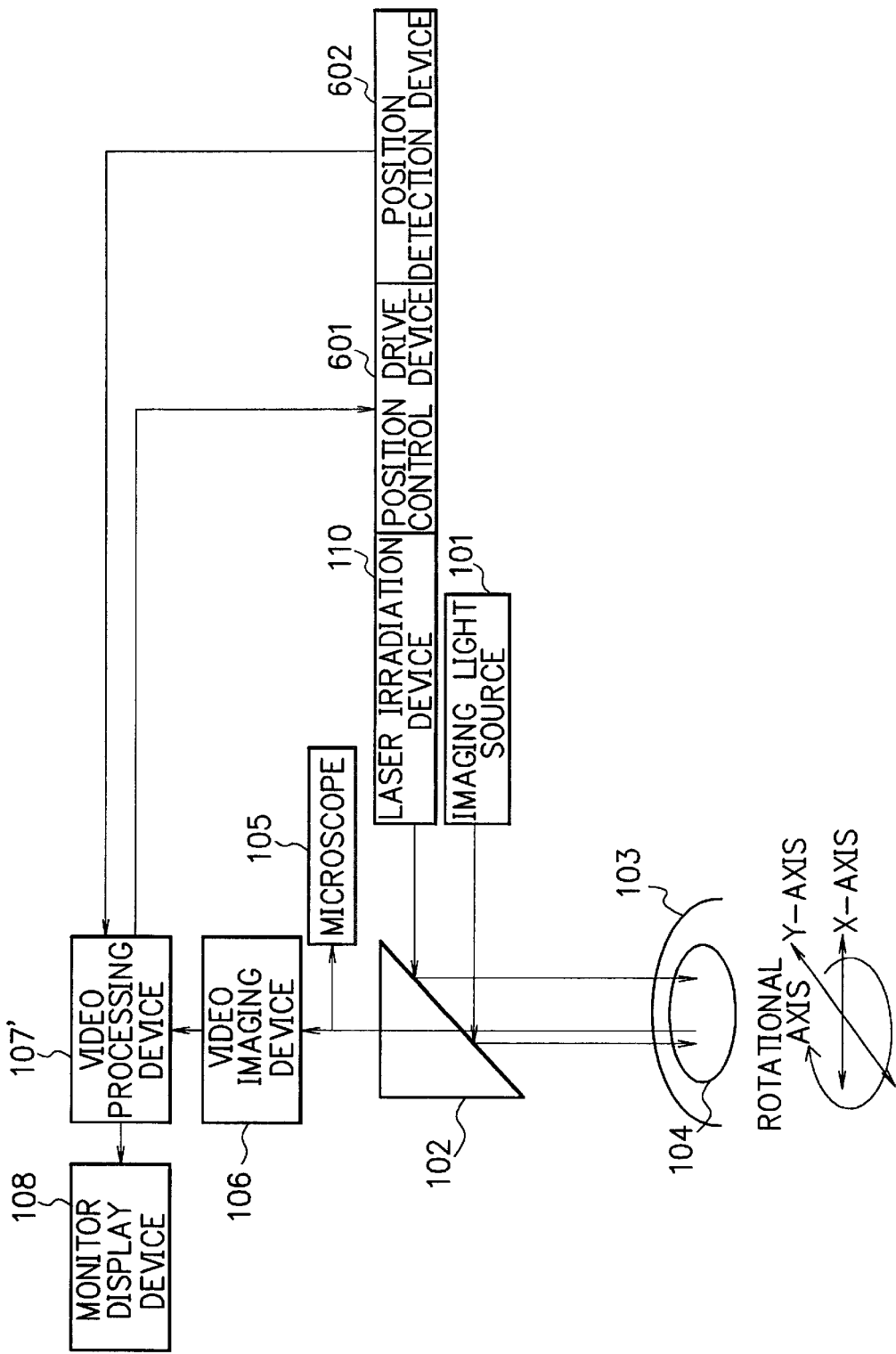
FIG. 6 is a block diagram showing the arrangement of a refraction correction apparatus to which a pupil measurement apparatus according to the second embodiment is applied.

FIG. 6 is a block diagram showing the arrangement of a refraction correction apparatus to which a pupil measurement apparatus according to the second embodiment is applied. The same reference numerals as in FIG. 1 denote blocks having the same functions in FIG. 6, and a repetitive description thereof will be omitted. A block that is not the same as in FIG. 1 but has a corresponding function is denoted by the same reference numeral with prime.

Referring to FIG. 6, a video processing device 107' supplies the video signal of the cornea 104, which is supplied from a video imaging device 106, to a monitor display device 108 and executes predetermined arithmetic processing for the video signal to calculate pieces of difference information of the cornea 104 with respect to the reference position, like the video processing device 107 shown in FIG. 1. The video processing device 107' controls a position drive control device 601 on the basis of the calculated difference information of the cornea 104 with respect to the reference position.

The position data of each stage, which is calculated by a position detection device 602, is supplied to the video processing device 107'.

The position drive control device 601 controls drive of movable stages (X-axis direction, Y-axis direction, and rotational direction) of a laser irradiation device 110 in accordance with drive signals supplied from the video processing device 107'. That is, the position drive control device 601 corrects shifts by moving the laser irradiation device 110 in the directions of X- and Y-axes and rotational axis on the basis of the shift amounts in the directions of X- and Y-axes and rotation in accordance with drive signals supplied from the video processing device 107'.

The position detection device 602 detects the positions of the movable stages (X-axis direction, Y-axis direction, and rotational direction) of the laser irradiation device 110 driven and controlled by the position drive control device 601 and supplies the detected position data to the video processing device 107'.

Figure 7:
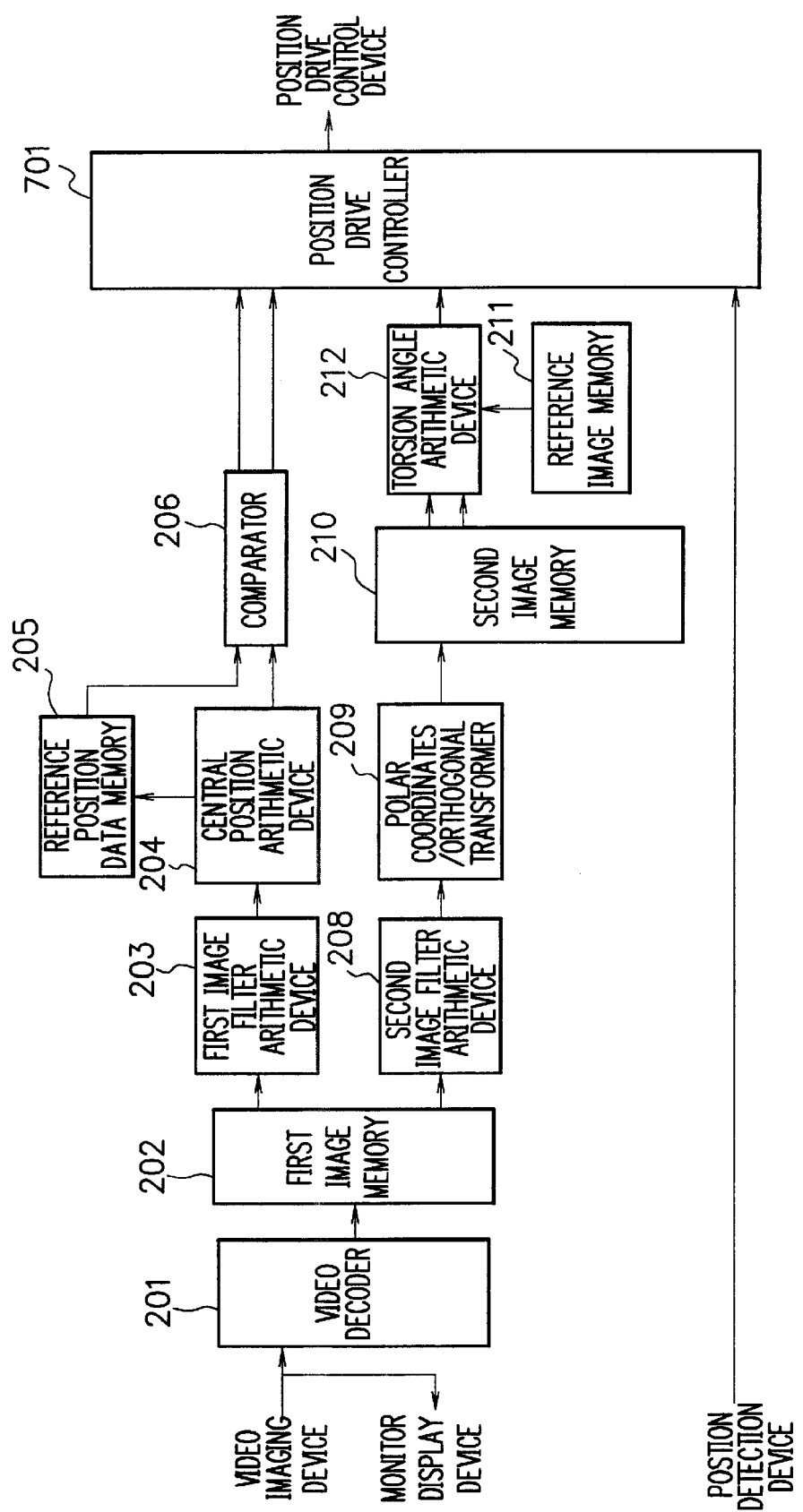
FIG. 7 is a block diagram showing the detailed arrangement of a video processing device.

FIG. 7 is a block diagram showing the detailed arrangement of the video processing device 107' shown in FIG. 6. The same reference numerals as in FIG. 2 denote blocks having the same functions in FIG. 7, and a repetitive description thereof will be omitted.

Referring to FIG. 7, a position drive controller 701 converts the difference value data between the X- and Y-coordinates of the central position of the pupil (cornea) based on the image data of the obtained eyeball image and the position data of the pupil (cornea) stored in a reference position data memory 205, which is supplied from a comparator 206, into drive signals for driving the X- and Y-axis movable stages of the laser irradiation device 110 shown in FIG. 6 and supplies the drive signals to the position drive control device 601.

The position drive controller 701 also converts the torsion angle of the cornea 104, which is calculated by a torsion angle arithmetic device 212, into a drive signal for driving the rotating movable stage of the laser irradiation device 110 shown in FIG. 6 and supplies the drive signal to the position drive control device 601.

Position data is supplied from the position detection device 602 shown in FIG. 6 to the position drive controller 701. In converting the pieces of difference information (shift amounts) of the cornea 104 with respect to the reference position, which are supplied from the comparator 206 and torsion angle arithmetic device 212, into drive signals for driving the movable stages of the laser irradiation device 110, the movable stages can be accurately driven by referring to the supplied position data.

FIG. 8 is a view showing the arrangements of the laser irradiation device 110, position drive control device 601, and position detection device 602. The same reference numerals as in FIG. 6 denote blocks having the same functions in FIG. 8, and a repetitive description thereof will be omitted.

Referring to FIG. 8, the laser irradiation device 110 is fixed on a rotating movable stage 803, X-axis movable stage 805, and Y-axis movable stage 807. A laser beam emitted from the laser irradiation device 110 is reflected by a mirror 801, focused by a lens 802, and output.

The rotating movable stage 803 moves in the rotational direction through a rotation driving section 804 on the basis of a rotating movable stage drive signal supplied from the position drive controller 701 in the video processing device 107' shown in FIG. 7.

The X-axis movable stage 805 moves in the X-axis direction through an X-axis driving section 806 on the basis of an X-axis movable stage drive signal supplied from the position drive controller 701 in the video processing device 107'.

The Y-axis movable stage 807 moves in the Y-axis direction through a Y-axis driving section 808 on the basis of a Y-axis movable stage drive signal supplied from the position drive controller 701 in the video processing device 107'.

The position drive control device 601 shown in FIG. 6 is constituted by the rotating movable stage 803, rotation driving section 804, X-axis movable stage 805, X-axis driving section 806, Y-axis movable stage 807, and Y-axis driving section 808.

A rotation angle detector 809, X-axis position detector 810, and Y-axis position detector 811 detect the positions of the rotating movable stage 803, X-axis movable stage 805, and Y-axis movable stage 807, respectively, and supply the detected position data to the video processing device 107'. When the positions of the movable stages 803, 805, and 807 are detected and the position data are supplied to the video processing device 107', the movable stages can be controlled by referring to the position data, and the laser beam emitted from the laser irradiation device 110 can be accurately scanned.

The position detection device 602 shown in FIG. 6 is constituted by the rotation angle detector 809, X-axis position detector 810, and Y-axis position detector 811.

Figures 9A, 9B:
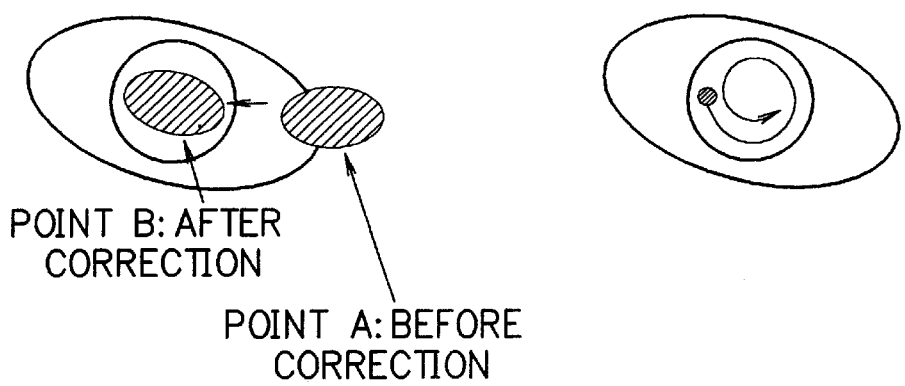
FIGS. 9A and 9B are views for explaining alignment between the position of a cornea and a laser beam irradiation position.

As described above, the refraction correction apparatus has the movable stages 803, 805, and 807 and the driving sections 804, 806, and 808 for them. For example, when the laser beam irradiation position before correction is at a point A on the cornea, as shown in FIG. 9A, the movable stages 803, 805, and 807 can be controlled through the driving sections 804, 806, and 808 on the basis of the difference information calculated by arithmetic processing by the video processing device 107' such that the laser beam irradiation position moves to a point B.

The beam diameter of the laser beam emitted from the laser irradiation device 110 is reduced. As shown in FIG. 9B, the intensity or irradiation count of the irradiation laser beam is adjusted and the surface of the cornea is scanned in an arbitrary direction (rotational direction in FIG. 9B) in accordance with the corneal shape. With this operation, the shaving amount of the cornea can be controlled, and more accurate refraction correction surgery can be realized. For example, a cornea can be shaved by adjusting the strength or irradiation count of an irradiation laser beam in accordance with the position on the cornea on the basis of contour line data obtained by a cornea analyzing apparatus.

As described above, according to the second embodiment, the video imaging device obtains the eyeball image of the cornea 104 using light emitted from an imaging light source 101 to the cornea 104. On the basis of the obtained eyeball image, the video processing device 107' calculates the X- and Y-axis shift amounts and torsion angle of the cornea 104 with respect to the reference position and adjusts the position of the laser irradiation device 110 on the basis of the calculated X- and Y-axis shift amounts and torsion angle such that the laser beam irradiation position on the cornea 104 is set at a predetermined position.

With this arrangement, in refraction correction surgery by the refraction correction apparatus, the position and torsion angle of the cornea of a patient can be accurately detected without forming any mark on the eyeball of the patient to measure the position of the cornea 104, and the position of the laser irradiation device 110 is adjusted on the basis of the detection result. For this reason, the operator can make the position of the cornea of the patient accurately match the laser beam irradiation position without any specific operation.

(Third Embodiment)

The third embodiment of the present invention will be described next.

In the third embodiment, a mask for forming a laser beam with which a cornea 104 is irradiated into an arbitrary shape is added to the second embodiment.

Figure 10:
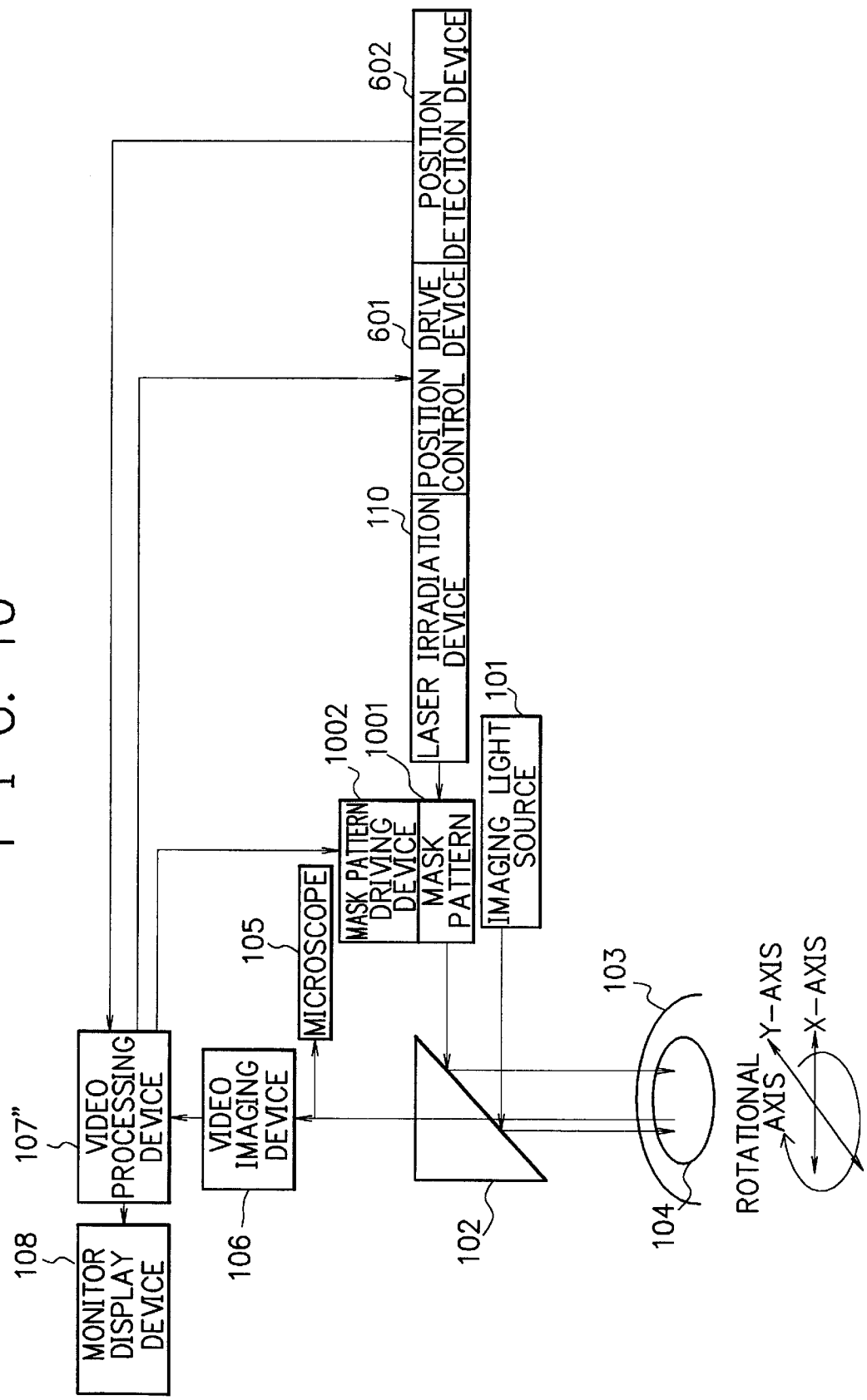
FIG. 10 is a block diagram showing the arrangement of a refraction correction apparatus to which a pupil measurement apparatus according to the third embodiment is applied.

FIG. 10 is a block diagram showing the arrangement of a refraction correction apparatus to which a pupil measurement apparatus according to the third embodiment is applied. The same reference numerals as in FIGS. 1 and 6 denote blocks having the same functions in FIG. 10, and a repetitive description thereof will be omitted. A block that is not the same as in FIGS. 1 and 6 but has a corresponding function is denoted by the same reference numeral with double prime.

Referring to FIG. 10, a video processing device 107" has a function of controlling a mask pattern driving device 1002 in addition to the function of the video processing device 107' shown in FIG. 6. The video processing device 107" analyzes the three-dimensional pattern on the cornea 104 on the basis of a received video signal of an eyeball image and outputs a mask pattern drive signal to the mask pattern driving device 1002.

On the basis of the mask pattern drive signal supplied from the video processing device 107", the mask pattern driving device 1002 selects a mask pattern 1001 from a plurality of mask patterns and lays out the mask pattern 1001 on the optical path of the laser beam. Hence, in refraction correction surgery, a laser irradiation device 110 can irradiate the cornea 104, through the mask pattern 1001 and half mirror 102, with a laser beam having an arbitrary shape corresponding to the mask pattern 1001 to shave the cornea.

FIG. 11 is a block diagram showing the detailed arrangement of the video processing device 107" shown in FIG. 10. The same reference numerals as in FIGS. 2 and 7 denote blocks having the same functions in FIG. 11, and a repetitive description thereof will be omitted.

Referring to FIG. 11, a first image memory 202' stores, as image data, the image signal of the video signal of the eyeball image separated by a video decoder 201 and supplies the image data to first to third image filter arithmetic devices 203, 208, and 1101.

The image data stored in the first image memory 202' and supplied to the third image filter arithmetic device 1101 is subjected to image processing such as noise removal and spatial filter by the third image filter arithmetic device 1101 having a filter and the like. The image data that has undergone image processing by the third image filter arithmetic device 1101 is supplied to a corneal shape analyzer 1102.

Upon receiving the image data that has undergone image processing, the corneal shape analyzer 1102 analyzes the three-dimensional pattern on the cornea 104 on the basis of the supplied image data and outputs analysis data to a mask pattern controller 1103. The mask pattern controller 1103 converts the analysis data supplied from the corneal shape analyzer 1102 into a mask pattern drive signal for driving the mask pattern driving device 1002 shown in FIG. 10 and supplies the mask pattern drive signal to the mask pattern driving device 1002.

The corneal shape analysis (analysis of the three-dimensional pattern on the cornea 104) by the corneal shape analyzer 1102 can be done by projecting stripes onto the cornea 104 and analyzing the image of the stripes. That is, for a normal eye having no distortion on the cornea 104, the stripes on the cornea indicate concentric circles at a predetermined interval, as shown in FIG. 12A. For an eye with near-sightedness or astigmatism, the stripes on the cornea indicate largely distorted circles, as shown in FIG. 12B. When the distorted circles are analyzed, the corneal distortion distribution on the cornea can be analyzed.

FIG. 13 is a view showing the arrangements of the laser irradiation device 110, position drive control device 601, position detection device 602, mask pattern drive control device 1002, and mask pattern 1001. The same reference numerals as in FIG. 8 denote blocks having the same functions in FIG. 13, and a repetitive description thereof will be omitted.

Referring to FIG. 13, a laser beam emitted from the laser irradiation device 110 through a mirror 801 and lens 802 is output through the mask pattern 1001. As the mask pattern 1001, one mask pattern 1001 is selected from a plurality of mask patterns on the basis of a mask pattern drive signal supplied from the mask pattern controller 1103 in the video processing device 107" shown in FIG. 11 to the mask pattern driving device 1002.

Figure 14:
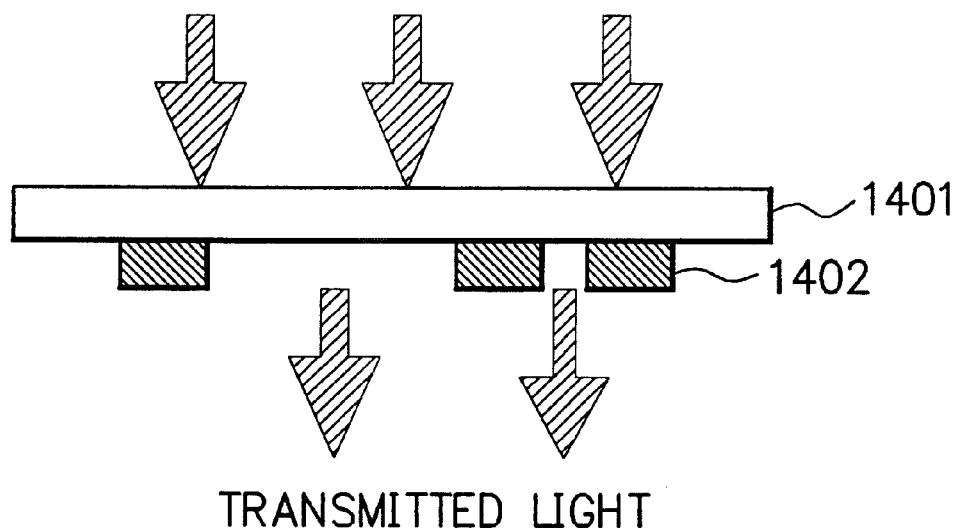
FIG. 14 is a view showing the structure of a mask pattern.

FIG. 14 is a view showing the structure of the mask pattern 1001.

Referring to FIG. 14, the mask pattern 1001 is obtained by forming a chromium pattern (mask) 1402 at each light-shielding portion on a transparent glass substrate 1401. A laser beam incident on the mask pattern 1001 is shielded at the portions of the chromium patterns 1402 and transmitted through the remaining portions to irradiate the cornea.

Figures 15A, 15B, 15C:
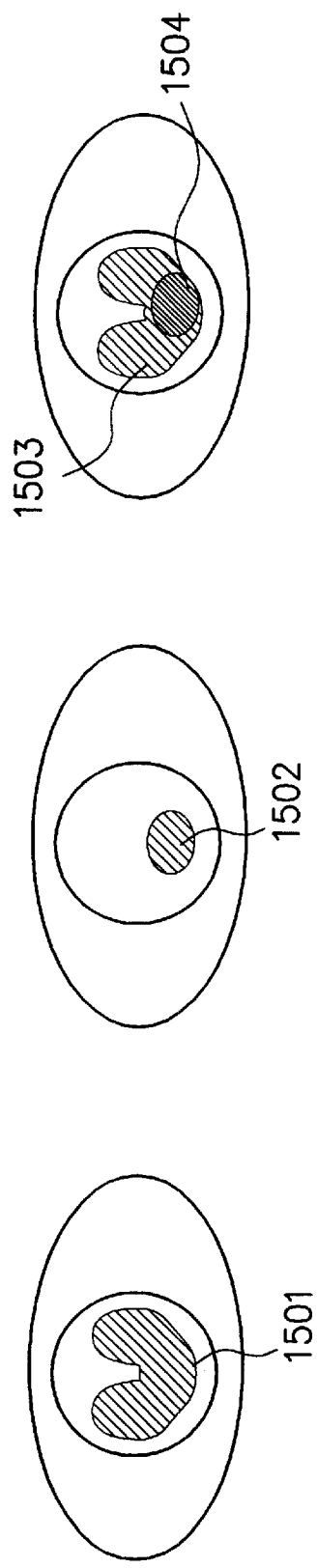
FIGS. 15A, 15B, and 15C are views for explaining a laser beam irradiation region when a mask pattern is used.
Figure 16:
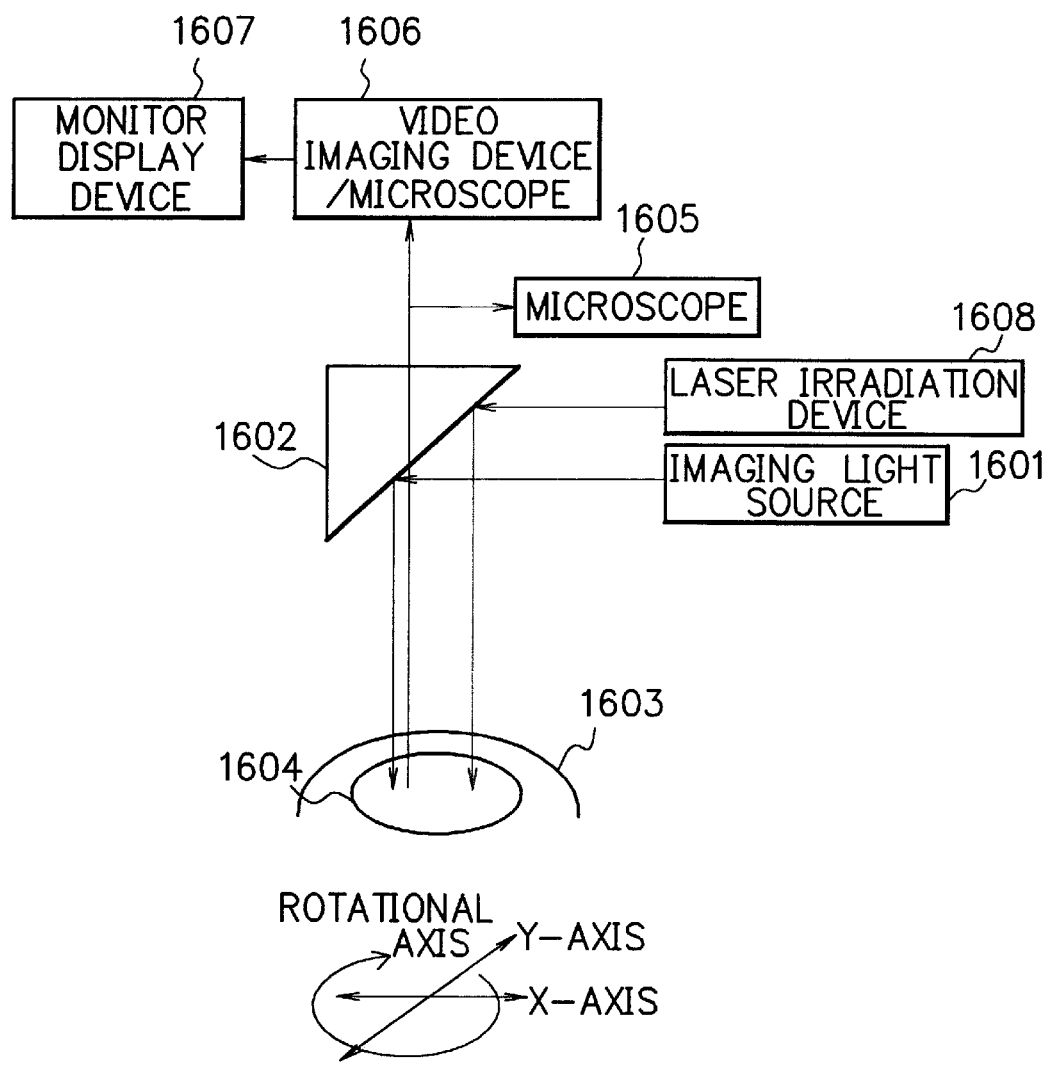
FIG. 16 is a block diagram showing the arrangement of a conventional refraction correction apparatus.
Figure 17A:
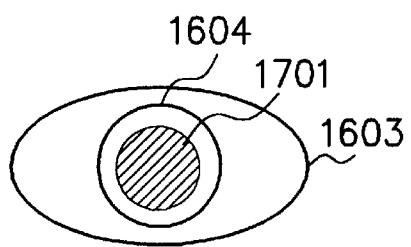
FIGS. 17A and 17B are views for explaining the position of a cornea and a laser beam irradiation position.
Figure 17B:
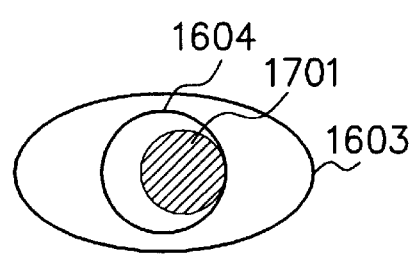
Figure 18A:
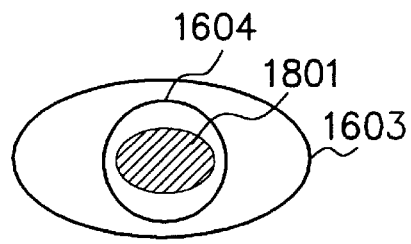
FIGS. 18A and 18B are views for explaining the position of a cornea and a laser beam irradiation position.
Figure 18B:
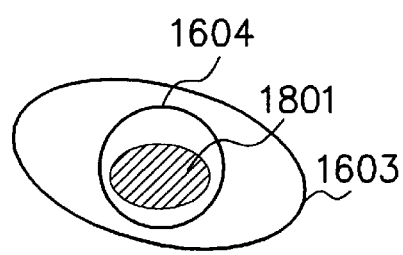

That is, when a cornea is irradiated with a laser beam having a beam shape corresponding to a pattern 1501 using the first mask pattern, as shown in FIG. 15A, and then, the cornea is irradiated with a laser beam having a beam shape corresponding to a pattern 1502 using the second mask pattern, as shown in FIG. 15B, the cornea can be shaved in the pattern shown in FIG. 15C. A point A of a pattern 1504 can be shaved deeply, and the portion of a pattern 1503 can be shaved shallowly.

As described above, according to the third embodiment, in addition to the effect of the second embodiment, the shape of the cornea 104 is analyzed by the video processing device 107" on the basis of an obtained eyeball image, a mask pattern 1001 complying with the corneal shape is selected by the mask pattern driving device 1002, and the cornea is irradiated with a laser beam by the laser irradiation device 110 through the selected mask pattern 1001. Hence, the cornea can be shaved in accordance with the shape of the patient's cornea, and more accurate refraction correction surgery can easily be executed.

In the above-described first to third embodiments, a cornea is irradiated with a laser beam through an optical system such as a lens. However, a cornea may be irradiated with a laser beam using an optical fiber tube.

When an optical fiber tube having a small diameter is used as the optical fiber tube, and movement of the optical fiber tube is controlled, a laser beam can be scanned as shown in FIG. 9B described above.

When a plurality of optical fiber tubes are used, and the light amount of a laser beam emitted from each optical fiber tube is controlled, the cornea shaving amount can be changed for each portion of the cornea, as in the above-described third embodiment. Hence, the same effect as in the third embodiment can be obtained.

In the above-described first to third embodiments, pieces of difference information of the cornea 104 with respect to the reference position, which are calculated by the video processing device 107, 107', or 107", are indicated or used to adjust the laser beam irradiation position. However, a storage unit for storing difference information may be arranged to store the difference information. Not the difference information but the X- and Y-coordinates of the central position of a cornea, which are input to the comparator 206, or a torsion angle calculated by the torsion angle arithmetic device 212 may be stored. In this case, the pupil measurement apparatus of the present invention can be used for a security system which recognizes a person by a pupil.

The above embodiments are mere examples of the present invention and should not be construed to limit the technical range of the present invention. That is, the present invention can be practiced in various forms without departing from its technical spirit and scope or major features.

As has been described above, according to the present invention, an eyeball is irradiated with light to obtain its image. On the basis of the obtained eyeball image, the position and torsion angle of the pupil in the eyeball are calculated. Piece of information related to the calculated position and torsion angle of the pupil are indicated or stored. Hence, the position and torsion angle of a cornea can be accurately measured only by executing arithmetic processing for the eyeball image obtained by obtaining the image of the eyeball without forming any mark on the eyeball to measure the position of the cornea or pupil in the eyeball.

In addition, the pieces of information related to the calculated position and torsion angle of the pupil are indicated or stored on the basis of the obtained eyeball image. When the pupil measurement apparatus is used for a refraction correction apparatus, the cornea position and the laser beam irradiation position can easily be accurately aligned without forming any mark on an eyeball of a patient to align the cornea position and the laser beam irradiation position. Hence, the operator is not required of any special skill and can easily do more accurate refraction correction surgery.

What is claimed is:

1. A pupil measurement apparatus comprising:

an imaging unit for obtaining an image of an eyeball;

an arithmetic processing unit for calculating a position and torsion angle of a pupil in the eyeball on the basis of the eyeball image obtained by said imaging unit; and an indicating unit for indicating pieces of information related to the position and torsion angle of the pupil and output from said arithmetic processing unit.

2. A pupil measurement apparatus comprising:

an imaging unit for obtaining an image of an eyeball;

an arithmetic processing unit for calculating a position and torsion angle of a pupil in the eyeball on the basis of the eyeball image obtained by said imaging unit; and a storage unit for storing pieces of information related to the position and torsion angle of the pupil and output from said arithmetic processing unit.

3. An apparatus according to claim 2, further comprising a comparison unit for comparing pieces of information related to a position and torsion angle of a pupil, which are stored in said storage unit in advance, with the pieces of information related to the position and torsion angle of the pupil and output from said arithmetic processing unit, and an indicating unit for indicating a comparison result by said comparison unit.

4. An apparatus according to claim 2, further comprising an input unit for inputting pieces of information related to a position and torsion angle of a pupil and causing said storage unit to store the information, a comparison unit for comparing the pieces of information related to the position and torsion angle of the pupil, which are input by said input unit and stored in said storage unit, with the pieces of information related to the position and torsion angle of the pupil and output from said arithmetic processing unit, and an indicating unit for indicating a comparison result by said comparison unit.

5. An apparatus according to claim 3, wherein said comparison unit outputs different values of the position and torsion angle of the pupil as the comparison result between the pieces of information related to the position and torsion angle of the pupil and stored in said storage unit and the pieces of information related to the position and torsion angle of the pupil and output from said arithmetic processing unit.

6. An apparatus according to claim 2, further comprising a comparison unit for comparing pieces of information related to a position and torsion angle of a pupil, which are stored in said storage unit in advance, with the pieces of information related to the position and torsion angle of the pupil and output from said arithmetic processing unit, and a stage control unit for controlling a position and torsion angle of a stage on the basis of a comparison result by said comparison unit.

7. An apparatus according to claim 2, further comprising an input unit for inputting pieces of information related to a position and torsion angle of a pupil and causing said storage unit to store the information, a comparison unit for comparing the pieces of information related to the position and torsion angle of the pupil, which are input by said input unit and stored in said storage unit, with the pieces of information related to the position and torsion angle of the pupil and output from said arithmetic processing unit, and a stage control unit for controlling a position and torsion angle of a stage on the basis of a comparison result by said comparison unit.

8. An apparatus according to claim 6, wherein said comparison unit outputs different values of the position and torsion angle of the pupil as the comparison result between the pieces of information related to the position and torsion angle of the pupil and stored in said storage unit and the pieces of information related to the position and torsion angle of the pupil and output from said arithmetic processing unit.

9. An apparatus according to claim 6, wherein said stage control unit comprises at least one of an X-axis moving unit, Y-axis moving unit, and rotating moving unit for moving the position of the stage in an X-axis direction, Y-axis direction, and rotational axis direction, respectively.

10. An apparatus according to claim 1, wherein said arithmetic processing unit executes one of polar coordinates/orthogonal transform processing and mutual correlation function processing using a mutual correlation function for the eyeball image obtained by said imaging unit.

11. An apparatus according to claim 2, wherein said arithmetic processing unit executes one of polar coordinates/orthogonal transform processing and mutual correlation function processing using a mutual correlation function for the eyeball image obtained by said imaging unit.

12. A pupil measurement apparatus comprising:

an imaging unit for obtaining an image of an eyeball;

a coordinate conversion unit for executing polar coordinates/orthogonal transform processing for the eyeball image obtained by said imaging unit; and an arithmetic processing unit for comparing the eyeball image orthogonally transformed by said coordinate conversion unit with a reference eyeball image stored in advance to calculate a position and torsion angle of a pupil in the eyeball.

13. An apparatus according to claim 12, wherein said arithmetic processing unit compares the eyeball image orthogonally transformed by said coordinate conversion unit with the reference eyeball image stored in advance using a correlation function.

14. A refraction correction apparatus comprising a pupil measurement apparatus, said pupil measurement apparatus comprising:

an imaging unit for obtaining an image of an eyeball;

an arithmetic processing unit for calculating a position and torsion angle of a pupil in the eyeball on the basis of the eyeball image obtained by said imaging unit; and an indicating unit for indicating pieces of information related to the position and torsion angle of the pupil and output from said arithmetic processing unit.

15. An apparatus according to claim 14, wherein said apparatus comprises a shape analyzing unit for analyzing a shape of the eyeball on the basis of the eyeball image obtained by said imaging unit, and a mask selection unit for selecting a mask pattern which changes a beam shape of a laser beam with which the eyeball is irradiated in accordance with the eyeball shape analyzed by said shape analyzing unit, and the eyeball is irradiated with the laser beam through the mask pattern selected by said mask selection unit.

16. A pupil measurement method wherein an image of an eyeball is obtained, a position and torsion angle of a pupil in the eyeball are calculated on the basis of the obtained eyeball image, and pieces of information related to the calculated position and torsion angle of the pupil are indicated.

17. A pupil measurement method wherein an image of an eyeball is obtained, a position and torsion angle of a pupil in the eyeball are calculated on the basis of the obtained eyeball image, and pieces of information related to the calculated position and torsion angle of the pupil are stored.

18. A pupil measurement method wherein an image of an eyeball is obtained, polar coordinates/orthogonal transform processing is executed for the obtained eyeball image, and the orthogonally transformed eyeball image is compared with a reference eyeball image stored in advance to calculate a position and torsion angle of a pupil in the eyeball.

* * * * *